(12) United States Patent
Jayet-Laraffe et al.

(10) Patent No.: US 8,765,159 B2
(45) Date of Patent: Jul. 1, 2014

(54) DATA MEDIUM HAVING BIOCIDAL PROPERTIES AND METHOD FOR MAKING SAME

(75) Inventors: Christiane Jayet-Laraffe, La Batie-Divisin (FR); Henri Rosset, Le Pin (FR)

(73) Assignee: Arjowiggins Security, Issy Lee Moulineaux (FR)

( * ) Notice: Subject to any disclaimer, the term of this patent is extended or adjusted under 35 U.S.C. 154(b) by 2154 days.

(21) Appl. No.: 10/510,347

(22) PCT Filed: Apr. 8, 2003

(86) PCT No.: PCT/FR03/01097
§ 371 (c)(1),
(2), (4) Date: Apr. 6, 2005

(87) PCT Pub. No.: WO03/084326
PCT Pub. Date: Oct. 16, 2003

(65) Prior Publication Data
US 2005/0175712 A1    Aug. 11, 2005

(30) Foreign Application Priority Data
Apr. 8, 2003  (FR) ...................................... 02 04363

(51) Int. Cl.
*A01N 25/00*    (2006.01)
*B05D 1/00*     (2006.01)

(52) U.S. Cl.
USPC .......................................... 424/405; 427/331

(58) Field of Classification Search
None
See application file for complete search history.

(56) References Cited

U.S. PATENT DOCUMENTS

| | | | |
|---|---|---|---|
| 3,738,995 A   | 6/1973 | Adams et al. | |
| 4,570,629 A * | 2/1986 | Widra ............................ | 604/304 |
| 4,908,209 A * | 3/1990 | McIntosh et al. .............. | 424/409 |
| 4,929,498 A   | 5/1990 | Suskind et al. | |
| 4,950,685 A   | 8/1990 | Ward | |
| 5,039,339 A * | 8/1991 | Phan et al. ..................... | 428/481 |
| 5,177,128 A * | 1/1993 | Lindemann et al. ........... | 524/44 |
| 5,217,576 A * | 6/1993 | Van Phan ....................... | 162/158 |
| 5,709,870 A * | 1/1998 | Yoshimura et al. ............ | 424/404 |
| 5,709,976 A * | 1/1998 | Malhotra ................. | 430/124.54 |
| 5,786,282 A   | 7/1998 | Carter et al. | |
| 6,197,805 B1   | 3/2001 | Smith | |
| 6,262,097 B1   | 7/2001 | Kovacevic | |
| 6,524,508 B1 * | 2/2003 | Ohnishi et al. ................ | 264/182 |
| 2004/0023008 A1 | 2/2004 | Rosset | |
| 2005/0175712 A1 * | 8/2005 | Jayet-Laraffe et al. ........ | 424/618 |

FOREIGN PATENT DOCUMENTS

| | | | |
|---|---|---|---|
| EP | 0059056 | | 9/1982 |
| EP | 0 251 132 A1 | | 1/1988 |
| EP | 0749848 | * | 12/1996 |
| JP | 51101124 | * | 9/1976 |
| WO | WO 99/42658 | * | 8/1999 ............ D21H 21/36 |
| WO | WO-99/42658 A1 | | 8/1999 |
| WO | WO-00/818577 A1 | | 4/2000 |
| WO | WO-00/49219 A1 | | 8/2000 |

OTHER PUBLICATIONS

Dreikom, "Agricultural Fungicides," (1994) and McEntee, "Industrial Antimicrobial Agents," (1995) in Kirk-Othmer Encyclopedia of Chemical Technology, Wiley, 2000 Online Edition.*
American Society for Testing and Materials, "Test method for determining the antimicrobial activity of immobilized antimicrobial agents under dynamic contact conditions," ASTM Method E 2149-01. Title Only.*
Association Francaise de Normalisation, "Characterization and measurement of the bacteriostatic activity of fabrics and polymer surfaces with antibacterial properties," AFNOR Method XP G39-010. Title Only.*
'Environmental impact of euro banknotes' from the European Central Bank, Dec. 20, 2007.*
Derwent English translation of JP 51101124 Sep. 1976.*
Kumar (Reactive and Functional Polymers. 2000; 46: 1-27).*
Patent Abstracts of Japan, vol. 1997, No. 07, Jul. 31, 1997.
Patent Abstracts of Japan, vol. 017, No. 216, Apr. 28, 1993 (C-1053).
Patent Abstracts of Japan, vol. 017, No. 513 (C-1111), Sep. 16, 1993.
Database WPI, Section Ch, Week 199728, Derwent Publications Ltd., London, GB; AN 1997-306854, XP002255632.
Patent Abstracts of Japan, vol. 1999, No. 08, Jun. 30, 1999.

* cited by examiner

*Primary Examiner* — Shanon A Foley
(74) *Attorney, Agent, or Firm* — Birch, Stewart, Kolasch & Birch, LLP

(57) ABSTRACT

The invention relates to an information carrier intended to be handled relatively frequently, characterized in that it contains at least one biocidal agent. This information carrier is in particular intended for the production of a banknote, of a passport, of a playing card, of a packaging, of a book or of a magazine. The invention also relates to the process for producing said information carrier, characterized in that at least one biocidal agent is incorporated into a basic carrier made of cellulosic and/or plastic materials.

34 Claims, No Drawings

DATA MEDIUM HAVING BIOCIDAL PROPERTIES AND METHOD FOR MAKING SAME

The invention relates to an information carrier intended to be handled relatively frequently, in particular a banknote.

More specifically, the invention relates to an information carrier exhibiting biocidal properties and to the process for producing it.

In modern societies, an increasingly large quantity of carriers intended to transmit information is handled daily and frequently by a large number of individuals, for whom no health control is required.

Now, these individuals, due to their environment, their professional activity, their entourage and the healthiness of their lifestyle, may be carrying germs, microbes and contaminating agents in general, which generate more or less serious epidemic and pandemic diseases.

Thus, the information carrier handled by these individuals is, in turn, liable to contain such pathogenic microorganisms. It then becomes an important vehicle for disseminating bacteria, yeast and fungi and can potentially cause infections in those who handle it.

In addition, recently, since the possibility of a terrorist act by bacteriological contamination of such information carriers is no longer to be neglected, the risk associated with handling such information carriers is becoming particularly sensitive.

As currency in commercial transactions, the banknote constitutes one of the information carriers most commonly handled throughout the world and, as a result, represents a potential threat to our health.

In many countries, the notes are handled billions of times during their circulation period.

They then become loaded up with microorganisms originating both from the ambient environment and from the human organism.

A study carried out by the Gazaga da Gama Filho Biochemical Research Institute in Brazil on the microbial contamination of Brazilian banknotes, and presented on Sep. 28, 2001, revealed in particular the presence of two specific contaminating agents, *Staphylococcus* sp and *Escherichia coli*.

The presence of these two microorganisms may, for the person who handles the banknote, result in various infections, which range from superficial diseases such as skin lesions, to styes, otitis, sinusitis, pharyngitis and other more serious ailments according to the sites of penetration, the amounts, the virulence of the sample, and the individual resistance.

In this context, the emerging tendency of banknotes having a more prolonged lifespan can only worsen, for the future, the risk of contamination associated with the handling of these notes.

Although it is not really new, the problem of the contamination of information carriers in general, and of banknotes in particular, has nevertheless up until now, to the applicant's knowledge, not been the subject of sufficient exhaustive investigations.

The study cited above mentions first of all the possibility of using a plastic material instead of the conventional cellulosic fibrous material for producing said banknotes.

The cellulosic fibrous material which has a tendency to absorb moisture is thought to promote the development of microorganisms within it.

Now, the study shows that this change reduces but does not eliminate the risk of contamination.

Other technical solutions have recently been disclosed in the prior art and in fact consist in treating the banknote paper with an antimicrobial agent.

Patent application WO 99/42658 envisions in particular the addition of a biguanide-based substantive antimicrobial agent.

Now, the applicant has noted that these prior solutions either do not completely satisfy the problem posed, since the antimicrobial agent does not have a complete, i.e. both antifungal and antibacteriological, biocidal action, or satisfies the problem posed at the cost of a substantial addition of antimicrobial agent.

These prior solutions therefore prove to be ineffective and too expensive.

In addition, antimicrobial agents are generally characterized by a degree of toxicity; adding them at a high dose can therefore prove to be unsuitable, or even dangerous.

The invention is aimed at providing an information carrier exhibiting both antifungal and antibacteriological properties, and not exhibiting the disadvantages of the prior art.

The applicant, after having tested many biocidal compositions, has succeeded, surprisingly, in solving the problems posed by treating the information carrier using a mixture of two biocidal agents, one having a fungistatic and/or fungicidal action, the other having a bacteriostatic and/or bactericidal action.

It has also proved to be the case that, among the antiseptic agents tested, some could exhibit the two actions at the same time.

Thus, the invention provides an information carrier intended to be handled relatively frequently, characterized in that it contains at least one biocidal agent.

Preferably, the information carrier contains at least one bacteriostatic and/or bactericidal agent and/or at least one fungistatic and/or fungicidal agent.

Preferably, at least one bacteriostatic and/or bactericidal agent is chosen from the compounds based on chitosan or chitin derivatives, on quaternary ammonium, on zinc zeolite, on silver ions and on triclosan.

Preferably, at least one bacteriostatic and/or bactericidal agent is based on didecyldimethylammonium chloride.

Preferably, at least one fungistatic and/or fungicidal agent is chosen from the compounds based on isothiazolin or isothiazolone derivatives, on chitosan or chitin derivatives, on quaternary ammonium, on zinc zeolite, on silver ions and on triclosan.

Preferably, at least one fungistatic and/or fungicidal agent is based on p-[(diiodomethyl)sulfonyl]toluol, on iodopropynyl butyl carbamate or on methyl-1H-benzimidazol-2-yl carbamate in the form of an aqueous dispersion.

Preferably, the quantity by dry weight of biocidal agent in the carrier is less than 1%, and preferably less than 0.2%.

Preferably, after one hour of dynamic contact of the carrier with a strain of *Escherichia coli* or of *Staphylococcus aureus*, the percentage decrease in the activity of the corresponding strains is greater than 99.9%, under the conditions defined by the ASTM E 2149-01 method.

Also preferably, after 24 hours of dynamic contact of the carrier with a strain of *Escherichia coli* or of *Staphylococcus aureus*, the antibacterial activity defined by the XPG 39010 method is negative.

In one embodiment, the information carrier is formed based on cellulosic materials, in particular paper.

In another embodiment, the information carrier is based on plastic materials.

Preferably, the information carrier is intended for the production of a banknote, of a passport, of a playing card, of a chipcard, of a packaging, of a book or of a magazine.

Another subject of the invention relates to a process for producing the information carrier mentioned above, characterized in that at least one biocidal agent is incorporated into a basic carrier made of cellulosic and/or plastic materials.

The incorporation of said biocidal agent into the basic carrier may be carried out in various ways:
- by immersing said basic carrier in a solution of said biocidal agent,
- by spraying said basic carrier with a solution of said biocidal agent,
- by printing said basic carrier using an ink containing said biocidal agent,
- by surfacing said basic carrier with a solution containing said biocidal agent and an aqueous surfacing agent, the aqueous surfacing agent preferably incorporating glycerol as plasticizer,
- by coating said basic carrier with a coating solution containing said biocidal agent,
- by depositing onto said basic carrier an overprint varnish containing said biocidal agent,
- by coating microcapsules or cyclodextrin containing said biocidal agent onto said basic carrier.

The following nonlimiting examples will make it possible to understand more fully the way in which the invention can be put into practice and its advantages.

COMPARATIVE EXAMPLE 1

A sheet of paper is formed on a paper machine, termed cylinder mould, with a wire cloth comprising a pattern for producing a watermark, it being possible for this paper to be suitable as paper for producing a banknote, in the following way:
- a paste of cotton fibers is suspended in water, this suspension is refined at 60° Schoepper-Riegler,
- a wet resistance agent, approximately 2.5% by dry weight of a poly(amide-amine-epichlorohydrin) resin, expressed relative to the cotton fibers, is added;
- small iridescent boards are also introduced into this suspension;
- during the formation of the sheet, a microprinted security thread, termed "window thread", is introduced according to known prior techniques, so that the thread appears in certain windows at the surface of the paper. A method that can be used to introduce this thread is described, for example, in patent EP 59056;
- after the sheet has been formed, it is surface-treated with a sizing agent in a size-press;
- the sheet is dried at around 100° C.

EXAMPLE 2

According to the Invention

A carrier according to Example 1 is used and is impregnated in an impregnating tank containing a composition prepared in aqueous medium, which comprises:
- 98 parts by commercial weight of a PVA binder,
- 2 parts by commercial weight of an isothiazolin-based biocidal agent sold under the reference "Microbiocide B43F" by the company Intace.

The concentration of biocidal agent relative to the total bath is set at 0.05%.

The pH of the impregnating composition is fixed at 6.6.

Once impregnated, the paper comprises a content by commercial weight of biocidal product of 0.037%, which corresponds to a content by dry weight of biocidal product in the paper of approximately 0.02%.

EXAMPLE 3

According to the Invention

A carrier according to Example 1 is used and is impregnated in an impregnating tank containing a composition prepared in aqueous medium, which comprises:
- 94 parts by commercial weight of a PVA binder,
- 6 parts by commercial weight of an isothiazolin-based biocidal agent sold under the reference "Microbiocide B43F" by the company Intace.

The concentration of biocidal agent relative to the total bath is set at 0.2%.

The pH of the impregnating composition is fixed at 6.6.

Once impregnated, the paper comprises a content by commercial weight of biocidal product of 0.14%, which corresponds to a content by dry weight of biocidal product in the paper of approximately 0.07%.

EXAMPLE 4

According to the Invention

A carrier according to Example 1 is used and is impregnated in an impregnating tank containing a composition prepared in aqueous medium, which comprises:
- 75 parts by commercial weight of a PVA binder,
- 25 parts by commercial weight of a chitosan-based biocidal agent sold under the reference "Chitogel" by the company France Chitine.

The concentration of biocidal agent relative to the total bath is set at 1.0%.

The pH of the impregnating composition is fixed at 6.8.

Once impregnated, the paper comprises a content by commercial weight of biocidal product of 0.75%, which corresponds to a content by dry weight of biocidal product in the paper of approximately 0.4%.

EXAMPLE 5

According to the Invention

A carrier according to Example 1 is used and is impregnated in an impregnating tank containing a composition prepared in aqueous medium, which comprises:
- 70 parts by commercial weight of a PVA binder,
- 30 parts by commercial weight of a chitosan-based biocidal agent sold under the reference "Chitosan 241" by the company France Chitine.

The concentration of biocidal agent relative to the total bath is set at 1.25%.

The pH of the impregnating composition is fixed at 5.2.

Once impregnated, the paper comprises a content by commercial weight of biocidal product of 0.925%, which corresponds to a content by dry weight of biocidal product in the paper of approximately 0.5%.

EXAMPLE 6

According to the Invention

A carrier according to Example 1 is used and is impregnated in an impregnating tank containing a composition prepared in aqueous medium, which comprises:

94 parts by commercial weight of a PVA binder,
6 parts by commercial weight of a didecyldimethylammonium chloride-based biocidal agent sold under the reference "Microbiocide B74" by the company Intace.

The concentration of biocidal agent B74 relative to the total bath is set at 0.2%.

The pH of the impregnating composition is fixed at 6.4.

Once impregnated, the paper comprises a content by commercial weight of biocidal product of 0.142%, which corresponds to a content by dry weight of biocidal product in the paper of approximately 0.07%.

EXAMPLE 7

According to the Invention

A carrier according to Example 1 is used and is impregnated in an impregnating tank containing a composition prepared in aqueous medium, which comprises:
88 parts by commercial weight of a PVA binder,
6 parts by commercial weight of a didecyldimethylammonium chloride-based biocidal agent sold under the reference "Microbiocide B74" by the company Intace,
6 parts by commercial weight of an isothiazolin-based biocidal agent sold under the reference "Microbiocide B43F" by the company Intace.

The concentrations of biocidal agent B74 and B43F relative to the total bath are set at 0.2%.

The pH of the impregnating composition is fixed at 6.07.

Once impregnated, the paper comprises a content by commercial weight of biocidal product of 0.28%, which corresponds to a content by dry weight of biocidal product in the paper of approximately 0.14%.

EXAMPLE 8

According to the Invention

A carrier according to Example 1 is used and is impregnated in an impregnating tank containing a composition prepared in aqueous medium, which comprises:
94 parts by commercial weight of a PVA binder,
6 parts by commercial weight of a 3-(methoxysilyl)propyldimethyloctadecyl-ammonium chloride-based biocidal agent sold under the reference "AEM 5772/5" by the company Devan.

The concentration of biocidal agent relative to the total bath is set at 0.2%.

The pH of the impregnating composition is fixed at 6.08.

Once impregnated, the paper comprises a content by commercial weight of biocidal product of 0.15%, which corresponds to a content by dry weight of biocidal product in the paper of approximately 0.08%.

EXAMPLE 9

According to the Invention

A carrier according to Example 1 is used and is impregnated in an impregnating tank containing a composition prepared in aqueous medium, which comprises:
86 parts by commercial weight of a PVA binder,
14 parts by commercial weight of a 3-(methoxysilyl)propyldimethyloctadecyl-ammonium chloride-based biocidal agent sold under the reference "AEM 5772/5" by the company Devan.

The concentration of biocidal agent relative to the total bath is set at 0.5%.

The pH of the impregnating composition is fixed at 6.08.

Once impregnated, the paper comprises a content by commercial weight of biocidal product of 0.37%, which corresponds to a content by dry weight of biocidal product in the paper of approximately 0.19%.

EXAMPLE 10

According to the Invention

A carrier according to Example 1 is used and is impregnated in an impregnating tank containing a composition prepared in aqueous medium, which comprises:
75 parts by commercial weight of a PVA binder,
25 parts by commercial weight of a 3-(methoxysilyl)propyldimethyloctadecyl-ammonium chloride-based biocidal agent sold under the reference "AEM 5772/5" by the company Devan.

The concentration of biocidal agent relative to the total bath is set at 1.0%.

The pH of the impregnating composition is fixed at 6.08.

Once impregnated, the paper comprises a content by commercial weight of biocidal product of 0.73%, which corresponds to a content by dry weight of biocidal product in the paper of approximately 0.37%.

EXAMPLE 11

According to the Invention

A carrier according to Example 1 is used and is impregnated in an impregnating tank containing a composition prepared in aqueous medium, which comprises:
50 parts by commercial weight of a PVA binder,
50 parts by commercial weight of a 3-(methoxysilyl)propyldimethyloctadecyl-ammonium chloride-based biocidal agent sold under the reference "AEM 5772/5" by the company Devan.

The concentration of biocidal agent relative to the total bath is set at 3.0%.

The pH of the impregnating composition is fixed at 6.08.

Once impregnated, the paper comprises a content by commercial weight of biocidal product of 2.22%, which corresponds to a content by dry weight of biocidal product in the paper of approximately 1.1%.

EXAMPLE 12

According to the Invention

A carrier according to Example 1 is used and is impregnated in an impregnating tank containing a composition prepared in aqueous medium, which comprises:
75 parts by commercial weight of a PVA binder,
25 parts by commercial weight of a sodium phenylphonolate-based biocidal agent sold under the reference "Bactolyse 74880" by the company Ondeo.

The concentration of biocidal agent relative to the total bath is set at 1.0%.

The pH of the impregnating composition is fixed at 6.6.

Once impregnated, the paper comprises a content by commercial weight of biocidal product of 0.72%, which corresponds to a content by dry weight of biocidal product in the paper of approximately 0.36%.

EXAMPLE 13

According to the Invention

A carrier according to Example 1 is used and is impregnated in an impregnating tank containing a composition prepared in aqueous medium, which comprises:
- 80 parts by commercial weight of a PVA binder,
- 20 parts by commercial weight of a isothiazolone derivative-based biocidal agent sold under the reference "Surfasept 74818" by the company Ondeo.

The concentration of biocidal agent relative to the total bath is set at 0.7%.

The pH of the impregnating composition is fixed at 6.6.

Once impregnated, the paper comprises a content by commercial weight of biocidal product of 0.525%, which corresponds to a content by dry weight of biocidal product in the paper of approximately 0.26%.

EXAMPLE 14

According to the Invention

A carrier according to Example 1 is used and is impregnated in an impregnation tank containing a composition prepared in aqueous medium, which comprises:
- 97 parts by commercial weight of PVA binder,
- 3 parts by commercial weight of a p-[(diiodomethyl)sulfonyl]toluol-based biocidal agent sold under the reference "Surfasept 74859" by the company Ondeo.

The concentration of biocidal agent relative to the total bath is set at 0.1%.

The pH of the impregnating composition is fixed at 6.8.

Once impregnated, the paper comprises a content by commercial weight of biocidal product of 0.075%, which corresponds to a content by dry weight of biocidal product in the paper of approximately 0.04%.

EXAMPLE 15

According to the Invention

A carrier according to Example 1 is used and is impregnated in an impregnating tank containing a composition prepared in aqueous medium, which comprises:
- 12.2 parts by commercial weight of a PVA binder,
- 86.7 parts by commercial weight of a polyurethane binder,
- 0.1 part by commercial weight of a didecyldimethylammonium chloride-based biocidal agent sold under the reference "Microbiocide B74" by the company Intace,
- 1.0 part by commercial weight of an iodopropynyl butyl carbamate-based biocidal agent sold under the reference "Fungitrol 420" by the company ISP.

The concentrations of biocidal agent B74 and Fungitrol 420 relative to the total bath are set, respectively, at 0.05% and 0.5%.

Once impregnated, the paper comprises a content by commercial weight of biocidal product, respectively, of 0.04% and of 0.4%, which corresponds to a content by dry weight of biocidal product in the paper, respectively, of approximately 0.02% and of approximately 0.08%.

EXAMPLE 16

According to the Invention

A carrier according to Example 1 is used and is surface-coated, using a size press, with a composition prepared in aqueous medium, which comprises:
- 12.3 parts by commercial weight of a PVA binder,
- 87.0 parts by commercial weight of a polyurethane binder,
- 0.1 part by commercial weight of a didecyldimethylammonium chloride-based biocidal agent sold under the reference "Microbiocide B74" by the company Intace,
- 0.7 part by commercial weight of an iodopropynyl butyl carbamate-based biocidal agent sold under the reference "Fungitrol 420" by the company ISP.

The concentrations of biocidal agent B74 and Fungitrol 420 relative to the total coating mixture are set, respectively, at 0.05% and 0.5%.

Once coated, the paper comprises a content by commercial weight of biocidal product, respectively, of 0.04% and of 0.27%, which corresponds to a content by dry weight of biocidal product in the paper, respectively, of approximately 0.02% and of approximately 0.05%.

EXAMPLE 17

According to the Invention

A carrier according to Example 1 is used and is impregnated in an impregnating tank containing a composition prepared in aqueous medium, which comprises:
- 98.4 parts by commercial weight of a PVA binder,
- 0.8 part by commercial weight of a didecyldimethylammonium chloride-based biocidal agent sold under the reference "Microbiocide B74" by the company Intace,
- 0.8 part by commercial weight of a p-[(diiodomethyl)sulfonyl]toluol-based biocidal agent sold under the reference "Surfasept 74859" by the company Ondeo.

The concentrations of biocidal agent B74 and Surfasept 74859 relative to the total bath are set, respectively, at 0.05% and 0.05%.

Once impregnated, the paper comprises a content by commercial weight of biocidal product, respectively, of 0.04% and of 0.04%, which corresponds to a content by dry weight of biocidal product in the paper, respectively, of approximately 0.02% and of approximately 0.02%.

EXAMPLE 18

According to the Invention

A carrier according to Example 1 is used and is surface-coated, using a size press, with a composition prepared in aqueous medium, which comprises:
- 98.4 parts by commercial weight of a PVA binder,
- 0.8 part by commercial weight of a didecyldimethylammonium chloride-based biocidal agent sold under the reference "Microbiocide B74" by the company Intace,
- 0.8 part by commercial weight of a p-[(diiodomethyl)sulfonyl]toluol-based biocidal agent sold under the reference "Surfasept 74859" by the company Ondeo.

The concentrations of biocidal agent B74 and Surfasept relative to the total coating mixture are set, respectively, at 0.05% and 0.05%.

Once coated, the paper comprises a content by commercial weight of biocidal product, respectively, of 0.04% and of 0.04%, which corresponds to a content by dry weight of biocidal product in the paper, respectively, of approximately 0.02% and of approximately 0.015%.

EXAMPLE 19

According to the Invention

A carrier according to Example 1 is used and is impregnated in an impregnating tank containing a composition prepared in aqueous medium, which comprises:

95.9 parts by commercial weight of a PVA binder,
0.8 part by commercial weight of a didecyldimethylammonium chloride-based biocidal agent sold under the reference "Microbiocide B74" by the company Intace,
3.3 parts by commercial weight of a methyl-1H-benzimidazol-2-yl carbamate-based biocidal agent sold under the reference "Surfasept 74843 P" by the company Aquazur P&P.

The concentrations of biocidal agent B74 and Surfasept 74843 P relative to the total bath are set, respectively, at 0.05% and 0.2%.

Once impregnated, the paper comprises a content by commercial weight of biocidal product, respectively, of 0.04% and of 0.15%, which corresponds to a content by dry weight of biocidal product in the paper, respectively, of approximately 0.02% and of approximately 0.07%.

EXAMPLE 20

According to the Invention

A carrier according to Example 1 is used and is surface-coated, using a size press, with a composition prepared in aqueous medium, which comprises:
96.1 parts by commercial weight of a PVA binder,
0.8 part by commercial weight of a didecyldimethylammonium chloride-based biocidal agent sold under the reference "Microbiocide B74" by the company Intace,
3.1 parts by commercial weight of a methyl-1H-benzimidazol-2-yl carbamate-based biocidal agent sold under the reference "Surfasept 74843 P" by the company Aquazur P&P.

The concentrations of biocidal agent B74 and Surfasept 74843 P relative to the total coating mixture are set, respectively, at 0.05% and 0.2%.

Once coated, the paper comprises a content by commercial weight of biocidal product, respectively, of 0.04% and of 0.15%, which corresponds to a content by dry weight of biocidal product in the paper, respectively, of approximately 0.02% and of approximately 0.06%.

EXAMPLE 21

According to the Invention

A carrier according to Example 1 is used and is impregnated in an impregnating tank containing a composition prepared in aqueous medium, which comprises:
60.9 parts by commercial weight of a PVA binder,
38.1 parts by commercial weight of a gelatin-type binder,
1.0 part by commercial weight of a biocidal agent based on a mixture of 1,2-benzoisothiazolin-3-one and of methyl-1-(butylcarbomyl)-2-benzimidazole carbamate sold under the reference "FBP-416" by the company IPEL.

The concentration of biocidal agent relative to the total bath is set at 1%.

Once impregnated, the paper comprises a content by commercial weight of biocidal product of 0.07%, which corresponds to a content by dry weight of biocidal product in the paper of approximately 0.04%.

Tests and Results:

The resistance of the carriers to the development of fungi and of bacteria was tested: this corresponds to both a fungistatic and bacteriostatic test.

The fungistatic test, which is the applicant's own test, uses the method presented in the appendix.

It is based both on ASTM standard G21-90 and on AFNOR standard NF X 41517.

The bacteriostatic test consists in evaluating the antibacterial resistance of the treated carriers to the growth of microbes under conditions of dynamic contact. The method used for Examples 1 to 14 is that described in ASTM standard E 2149-01.

It consists in bringing the treated carrier into contact in a bacterial suspension comprising the strain to be studied, with agitation for, respectively, one hour and 24 hours.

The antibacterial activity is defined by the determination, in the bacterial suspension, of the number of colony-forming units before and after the test.

A loss of microbial activity is deduced therefrom, and is expressed as a percentage. The method used for Examples 15 to 21 is that described in standard XPG 39010.

It consists in bringing the treated carrier into contact in a bacterial suspension comprising the strain to be studied, with agitation for, respectively, 0 hour and 24 hours.

The antibacterial activity is defined by the determination, in the bacterial suspension, of the number of colony-forming units before and after the test.

An antibacterial activity A is deduced therefrom, which activity is defined by the following formula:

$$A = \text{mean of } \log(E24i)\text{values} - \text{mean of } \log(E0i)\text{values},$$

where E24i corresponds to the number of CFUs present on the test piece i at 24 h and E0i corresponds to the number of CFUs present on the test piece i just after it has been brought into contact with the antibacterial agent.

In Examples 1 to 14, the strain studied was *Escherichia coli*.

In Examples 15 to 21, the strain studied was *Staphylococcus aureus*.

The results with these two series of tests were combined in Table 1, for Examples 1 to 14, and in Table 2, for Examples 15 to 21.

Some examples, for which the antibacterial activity was rather weak, were not subjected to bacteriostatic tests.

It is noted that, for the series of Examples 1 to 14, Examples 6 and 7 are particularly suitable for combating the growth of *Eschérichia coli* strains. Compared to Examples 8 to 11, using another quaternary ammonium-based biocidal agent, they act rapidly and effectively at very low concentrations.

As regards the fungistatic activity, only Examples 13 and 14 provide a complete absence of development of fungi.

They are, on the other hand, ineffective against bacterial development.

A conjugated addition of the biocidal agent of Example 6 and of Example 14 is therefore particularly recommended for obtaining complete biocidal protection for said information carrier.

As regards the series of Examples 15 to 21, it is noted that all the biocidal agents used have quite a thorough bactericidal action, given that all the CFUs present on the paper samples disappeared 24 hours after it had been brought into contact with said agents.

Their fungistatic potency is also considerable, with the exception of Example 21, for which the applicant observes better results at higher concentrations.

The examples given are obviously not exhaustive and other basic carriers and other biocidal agents may be envisioned without departing from the field of protection of the patent.

In particular, the basic carrier may be a high-durability security paper which is the subject of patent application FR 2 814 476, a printing/writing paper, a tracing paper or a plastic note.

TABLE 1

| EXAMPLE No. | FUNGISTATIC TEST ON INERT MEDIUM | | | | BACTERIOSTATIC TEST percentage decrease in *Escherichia coli* activity | |
|---|---|---|---|---|---|---|
| | 7 DAYS | | 14 DAYS | | | |
| | Front | Back | Front | Back | after 1 h | after 24 h |
| 1 | 4 | 4 | 4 | 4 | 0 | 0 |
| 2 | 4 | 4 | 4 | 4 | | |
| 3 | 2 | 3 | 4 | 4 | | |
| 4 | 4 | 4 | 4 | 4 | 80.6 | >99.9 |
| 5 | 4 | 4 | 4 | 4 | 80.6 | >99.9 |
| 6 | 1 | 1 | 3 | 3 | >99.9 | >99.9 |
| 7 | 1 | 1 | 3 | 2 | >99.9 | >99.9 |
| 8 | 4 | 4 | 4 | 4 | 87.4 | >99.9 |
| 9 | 4 | 4 | 4 | 4 | 92.7 | >99.9 |
| 10 | 4 | 4 | 4 | 4 | 99.5 | >99.9 |
| 11 | 4 | 4 | 4 | 4 | >99.9 | >99.9 |
| 12 | 1 | 1 | 3 | 4 | | |
| 13 | 0 | 0 | 1 | 3 | | |
| 14 | 0 | 0 | 0 | 0 | | |

TABLE 2

| EXAMPLE No. | FUNGISTATIC TEST ON INERT MEDIUM | | | | BACTERIOSTATIC TEST | | | | Antibacterial activity A |
|---|---|---|---|---|---|---|---|---|---|
| | 7 DAYS | | 14 DAYS | | After 0 hours | | After 24 hours | | |
| | Front | Back | Front | Back | E0i | Log(E0i) | E24i | Log(E24i) | |
| 15 | 0 | 0 | 0 | 1 | 34100 | 4.53 | 0 | 0 | −4.53 |
| 16 | 0 | 0 | 1 | 0 | 7200 | 3.86 | 0 | 0 | −3.86 |
| 17 | 0 | 0 | 0 | 0 | 6300 | 3.80 | 0 | 0 | −3.80 |
| 18 | 1 | 1 | 3 | 3 | 189000 | 5.28 | 0 | 0 | −5.28 |
| 19 | 0 | 0 | 0 | 0 | 89000 | 4.95 | 0 | 0 | −4.95 |
| 20 | 0 | 0 | 1 | 1 | 49500 | 4.69 | 0 | 0 | −4.69 |
| 21 | 2 | 2 | 2 | 3 | 100000 | 5 | 0 | 0 | −5 |

Fungistatic Test

Principle: the paper to be tested is placed on a sterile Petri dish, on an inert medium, providing the inside of the dish with moisture, and then seeded with an inoculum prepared with a mixture of activated strains.

The dishes are placed in an incubator at 28° C. for 14 days and are observed at 14 days.

I—Strains Used:
10 Different Strains are Used:
1) *Chaetomium globosum*
2) *Myrothecium verrucaria*
3) *Stachybotrys atra*
4) *Cladosporium herbarum*
5) *Penicillium funicolosum*
6) *Trichoderma viride*
7) *Aspergillus niger*
8) *Aspergillus flavus*
9) *Aspergillus ustus*
10) *Paecilomyces variotii*

II—Storage of the Strains:
The strains are stored in a refrigerator at between 3 and 5° C.

III—Trial:
A) Activation of the Strains

When a trial is programmed, the first operation consists in activating the strains, two weeks (between 14 and 16 days) before the test. In fact, since the strains are stored on a relatively non-nutritive medium, it is necessary to make them more active by culturing them on a more nutritive medium.

According to the strains, two media are used:

For *Chaetomium globosum, Stachybotrys atra, Cladosporium herbarum* and *Penicillium funicolosum*, the following medium is used:

| | |
|---|---|
| Oat flakes | 50 g |
| Branched agar | 20 g |
| Distilled water | 1000 ml |

For the other strains, the following medium is used:

| | |
|---|---|
| Moser malt | 40 g |
| Mycological peptone | 0.5 g |
| Branched agar | 20 g |
| Distilled water | 1000 ml |

After 14 days, the strains are ready to be used.

B) Trial Media:
The medium is made up of:

| | |
|---|---|
| $NH_4NO_3$ | 3 g |
| KCl | 0.25 g |
| $MgSO_4\ 7H_2O$ | 0.5 g |
| $KH_2PO_4$ | 1 g |
| Agar | 20 g |
| Water | 1000 ml |

The pH is adjusted to approximately 5.5.

It is an inert medium serving as a support for the test pieces.

The medium is sterilized for 30 minutes in a pressure cooker, in Erlenmeyer flasks with cottonwool stoppers, and then the agar is poured into sterile polystyrene dishes.

In parallel, an empty Erlenmeyer flask covered with a gauze and then with a cottonwool stopper and an Erlenmeyer flask containing 100 ml of distilled water are sterilized.

C) Initiating the Test

A minimum of two test pieces/face, i.e. four dishes/trial, are cut out.

They are placed separately in a small plastic bag until transfer into dishes.

The test pieces are disks 33 mm in diameter that are cut out using a hole-punch.

The test pieces are placed at the center of the dish on the agar, using forceps under rules of asepsis.

The dishes are labeled.

Preparation of the Inoculum:

The strains are mixed.

The concentration of each strain should be approximately $10^6$ ($10^5$ to $10^7$), measured with a Thoma cell, which represents 1 to 10 conidia per square.

After verification of the concentration, the strains are mixed in the sterile empty Erlenmeyer flask and then in the spraying device sterilized beforehand with alcohol.

D) Inoculation

Using the spraying device, the entire surface is inoculated, i.e. test piece+agar.

E) Incubation

This is left to act for 14 days at 28° C. with water saturation.

IV—Results

The invasion of the paper is characterized using a marking system:

0=>no attack
1=>traces of fungal development
2=>slight development (10 to 30%)
3=>moderate development (30 to 60%)
4=>strong development (>60%).

The invention claimed is:

1. A process for producing an information carrier, intended to be handled relatively frequently and selected from the group consisting of a banknote, a passport, a playing card, a chipcard, a packaging, a book, and a magazine, comprising the step of:
  incorporating at least two biocidal agents into the information carrier made of at least one material selected from cellulosic and plastic materials;
  wherein at least a first biocidal agent is selected from the group consisting of bacteriostatic and bactericidal agents, and at least a second biocidal agent is selected from the group consisting of fungistatic and fungicidal agents;
  wherein the first biocidal agent comprises didecyldimethylammonium chloride or silver ions and the second biocidal agent comprises p-[(diiodomethyl)sulfonyl]toluol in the form of an aqueous dispersion or iodopropynyl butyl carbamate in the form of an aqueous dispersion; and
  wherein the incorporation of said biocidal agents is carried out by surfacing said information carrier with a solution containing said biocidal agents.

2. The production process of claim 1, wherein the first biocidal agent comprises silver ions.

3. The production process of claim 1, wherein the first biocidal agent comprises didecyldimethylammonium chloride.

4. The production process of claim 1, wherein the second biocidal agent comprises p-[(diiodomethyl)sulfonyl]toluol in the form of an aqueous dispersion.

5. The production process of claim 1, wherein the second biocidal agent comprises iodopropynyl butyl carbamate in the form of an aqueous dispersion.

6. The production process of claim 1, wherein the quantity by dry weight of biocidal agent in the carrier is less than 1%.

7. The production process of claim 1, wherein the information carrier comprises cellulosic materials.

8. The production process of claim 1, wherein the information carrier comprises plastic materials.

9. The production process of claim 1, wherein the incorporation of said biocidal agents is also carried out by immersing said information carrier in a solution of said biocidal agents.

10. The production process of claim 1, wherein the incorporation of said biocidal agents is also carried out by spraying said information carrier with a solution of said biocidal agents.

11. The production process of claim 1, wherein the incorporation of said biocidal agents is also carried out by printing said information carrier using an ink containing said biocidal agents.

12. The production process of claim 1, wherein the incorporation of said biocidal agents is also carried out by surfacing said information carrier with a solution containing said biocidal agents and an aqueous surfacing agent, wherein the aqueous surfacing agent includes glycerol as a plasticizer.

13. The production process of claim 1, wherein the incorporation of said biocidal agents is also carried out by coating said information carrier with a coating solution containing said biocidal agents.

14. The production process of claim 1, wherein the incorporation of said biocidal agents is also carried out by depositing onto said information carrier an overprint varnish containing said biocidal agents.

15. The production process of claim 1, wherein the incorporation of said biocidal agents is also carried out by coating microcapsules or cyclodextrin containing said biocidal agents onto said information carrier.

16. The production process of claim 1, wherein said first biocidal agent is a bactericidal agent and said second biocidal agent is a fungicidal agent.

17. The production process of claim 1, wherein said first biocidal agent comprises didecyldimethylammonium chloride and said second biocidal agent comprises p-[(diiodomethyl)sulfonyl]toluol in the form of an aqueous dispersion.

18. The production process of claim 1, wherein said first biocidal agent comprises didecyldimethylammonium chloride and said second biocidal agent comprises iodopropynyl butyl carbamate in the form of an aqueous dispersion.

19. The production process of claim 1, wherein said first biocidal agent comprises silver ions and said second biocidal agent comprises iodopropynyl butyl carbamate in the form of an aqueous dispersion.

20. A method for decreasing the contamination of an information carrier, intended to be handled relatively frequently and selected from the group consisting of a banknote, a passport, a playing card, a chipcard, a packaging, a book, and a magazine, comprising the step of:
  incorporating at least two biocidal agents into the information carrier made of at least one material selected from cellulosic and plastic materials;
  wherein at least a first biocidal agent is selected from the group consisting of bacteriostatic and bactericidal agents, and at least a second biocidal agent is selected from the group consisting of fungistatic and fungicidal agents; and
  wherein the first biocidal agent comprises didecyldimethylammonium chloride or silver ions, and the second biocidal agent comprises p-[(diiodomethyl)sulfonyl]toluol in the form of an aqueous dispersion or iodopropynyl butyl carbamate in the form of an aqueous dispersion.

21. The production process of claim 1, wherein the quantity by dry weight of biocidal agent in the carrier is less than 0.2%.

22. An information carrier, intended to be handled relatively frequently and selected from the group consisting of a banknote, a passport, a playing card, a chipcard, a packaging, a book, and a magazine, said information carrier containing at least two biocidal agents, at least a first biocidal agent being selected from the group consisting of bacteriostatic and bactericidal agents, and at least a second biocidal agent being selected from the group consisting of fungistatic and fungicidal agents;

wherein the first biocidal agent comprises didecyldimethylammonium chloride or silver ions, and the second biocidal agent comprises p-[(diiodomethyl)sulfonyl]toluol in the form of an aqueous dispersion or iodopropynyl butyl carbamate in the form of an aqueous dispersion.

23. The information carrier as claimed in claim 22, wherein the first biocidal agent comprises silver ions.

24. The information carrier as claimed in claim 22, wherein the first biocidal agent comprises didecyldimethylammonium chloride.

25. The information carrier as claimed in claim 22, wherein the second biocidal agent comprises p-[(diiodomethyl)sulfonyl]toluol in the form of an aqueous dispersion.

26. The information carrier as claimed in claim 22, wherein the second biocidal agent comprises iodopropynyl butyl carbamate in the form of an aqueous dispersion.

27. The information carrier as claimed in claim 22, wherein the quantity by dry weight of biocidal agent in the carrier is less than 1%.

28. The information carrier as claimed in claim 22, wherein the information carrier comprises cellulosic materials.

29. The information carrier as claimed in claim 22, wherein the information carrier comprises plastic materials.

30. The information carrier as claimed in claim 22, wherein said first biocidal agent is a bactericidal agent and said second biocidal agent is a fungicidal agent.

31. The information carrier as claimed in claim 22, wherein said first biocidal agent comprises didecyldimethylammonium chloride and said second biocidal agent comprises p-[(diiodomethyl)sulfonyl]toluol in the form of an aqueous dispersion.

32. The information carrier as claimed in claim 22, wherein said first biocidal agent comprises didecyldimethylammonium chloride and said second biocidal agent comprises iodopropynyl butyl carbamate in the form of an aqueous dispersion.

33. The information carrier as claimed in claim 22, wherein said first biocidal agent comprises silver ions and said second biocidal agent comprises iodopropynyl butyl carbamate in the form of an aqueous dispersion.

34. The information carrier as claimed in claim 22, wherein the quantity by dry weight of biocidal agent in the carrier is less than 0.2%.

* * * * *

UNITED STATES PATENT AND TRADEMARK OFFICE
CERTIFICATE OF CORRECTION

PATENT NO. : 8,765,159 B2
APPLICATION NO. : 10/510347
DATED : July 1, 2014
INVENTOR(S) : Christiane Jayet-Laraffe et al.

Page 1 of 1

It is certified that error appears in the above-identified patent and that said Letters Patent is hereby corrected as shown below:

ON THE TITLE PAGE:

At item (30), correct the Foreign Application Priority Data to read as follows:

--Apr. 8, 2002    (FR)    ........................    02 04363--.

Signed and Sealed this
Thirtieth Day of December, 2014

Michelle K. Lee
*Deputy Director of the United States Patent and Trademark Office*